(12) United States Patent
Segner et al.

(10) Patent No.: US 6,662,034 B2
(45) Date of Patent: Dec. 9, 2003

(54) MAGNETICALLY GUIDABLE ELECTROPHYSIOLOGY CATHETER

(75) Inventors: Garland L. Segner, Watertown, MN (US); Roger N. Hastings, Maple Grove, MN (US); Michael Eng, Shoreview, MN (US)

(73) Assignee: Stereotaxis, Inc., St. Louis, MO (US)

( * ) Notice: Subject to any disclaimer, the term of this patent is extended or adjusted under 35 U.S.C. 154(b) by 19 days.

(21) Appl. No.: 09/840,311

(22) Filed: Apr. 23, 2001

(65) Prior Publication Data

US 2002/0058866 A1 May 16, 2002

Related U.S. Application Data

(63) Continuation-in-part of application No. 09/771,954, filed on Jan. 29, 2001.

(51) Int. Cl.[7] ................................................. A61B 5/04
(52) U.S. Cl. ........................................ 600/373; 606/41
(58) Field of Search ................................. 600/374, 373; 606/41–50; 604/21

(56) References Cited

U.S. PATENT DOCUMENTS

| | | | |
|---|---|---|---|
| 3,358,676 A | * 12/1967 | Frei et al. ..................... | 600/12 |
| 4,162,679 A | 7/1979 | Reenstierna | |
| 4,809,713 A | 3/1989 | Grayzel | |
| 5,391,199 A | 2/1995 | Ben-Haim | |
| 5,429,131 A | * 7/1995 | Scheinman et al. ........... | 606/41 |
| 5,443,489 A | 8/1995 | Ben-Haim | |
| 5,480,422 A | 1/1996 | Ben-Haim | |
| 5,546,951 A | 8/1996 | Ben-Haim | |
| 5,558,091 A | 9/1996 | Acker et al. | |
| 5,568,809 A | 10/1996 | Ben-Haim | |
| 5,694,945 A | 12/1997 | Ben-Haim | |
| 5,713,946 A | 2/1998 | Ben-Haim | |
| 5,718,241 A | 2/1998 | Ben-Haim et al. | |
| 5,729,129 A | 3/1998 | Acker | |
| 5,738,096 A | 4/1998 | Ben-Haim | |
| 5,833,608 A | 11/1998 | Acker | |
| 5,840,025 A | 11/1998 | Ben-Haim | |
| 5,882,346 A | 3/1999 | Pomeranz et al. | |
| 5,925,301 A | * 7/1999 | Johnson et al. ............. | 600/374 |
| 6,015,414 A | * 1/2000 | Werp et al. .................. | 606/108 |
| 6,017,338 A | * 1/2000 | Brucker et al. ............. | 606/122 |
| 6,056,745 A | * 5/2000 | Panescu et al. ............... | 606/42 |
| 6,063,078 A | 5/2000 | Wittkampf | |
| 6,104,944 A | * 8/2000 | Martinelli .................... | 128/899 |
| 6,217,574 B1 | * 4/2001 | Webster ........................ | 606/41 |
| 6,292,678 B1 | * 9/2001 | Hall et al. ..................... | 606/41 |
| 6,298,257 B1 | * 10/2001 | Hall et al. .................... | 600/407 |
| 6,385,472 B1 | * 5/2002 | Hall et al. ..................... | 606/41 |

OTHER PUBLICATIONS

Ritter, et al., US Patent Application Publication No. US 2001/0038683 A1, for Open Field System for Magnetic Surgery, filed Apr. 25, 2001.

U.S. patent application Ser. No. 09/771,954, entitled "Electrophysiology Catheter", filed Jan. 29, 2001, (co-pending application, being examined by Examiner Kathryn P. Ferko).

* cited by examiner

Primary Examiner—Roy D. Gibson
Assistant Examiner—Henry M. Johnson, III
(74) Attorney, Agent, or Firm—Harness, Dickey & Pierce, P.L.C.

(57) ABSTRACT

An electrophysiology catheter includes a tube having a proximal end, a distal end, and a lumen therebetween. The tube is preferably comprised of multiple sections of different flexibility, arranged so that the flexibility of the catheter increases from the proximal end to the distal end. There is a first generally hollow electrode member at the distal end. A magnetically responsive element is disposed at least partially in the hollow end electrode, for aligning the distal end of the catheter with an externally applied magnetic field. The hollow end electrode can have openings for delivering irrigating fluid, and/or a sleeve can be provided around the tube to create an annular space for the delivering of irrigating fluid. A temperature sensor can be provided to control the operation of the catheter. A localization coil can also be provided to sense the position and orientation of the catheter.

2 Claims, 6 Drawing Sheets

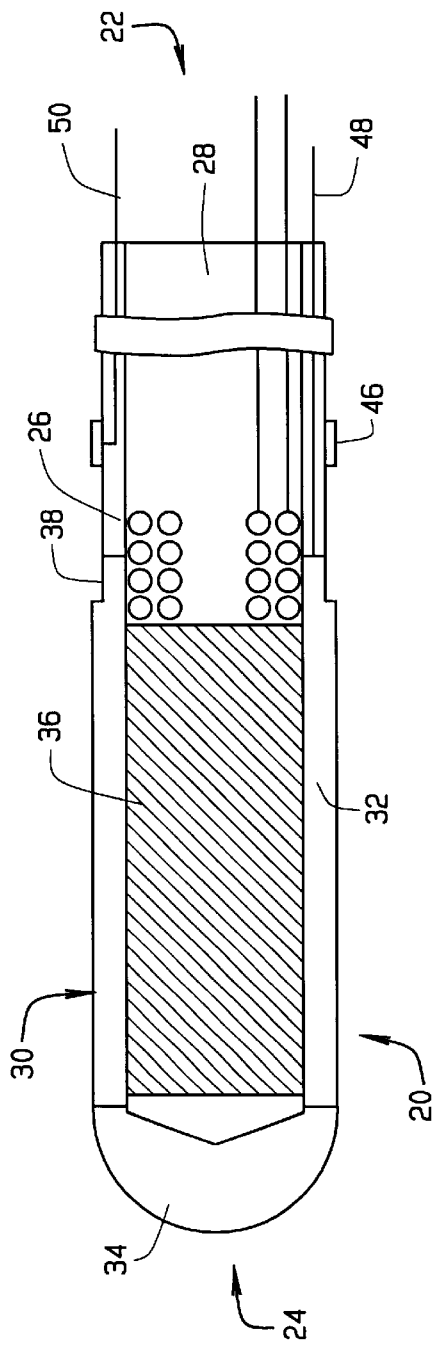
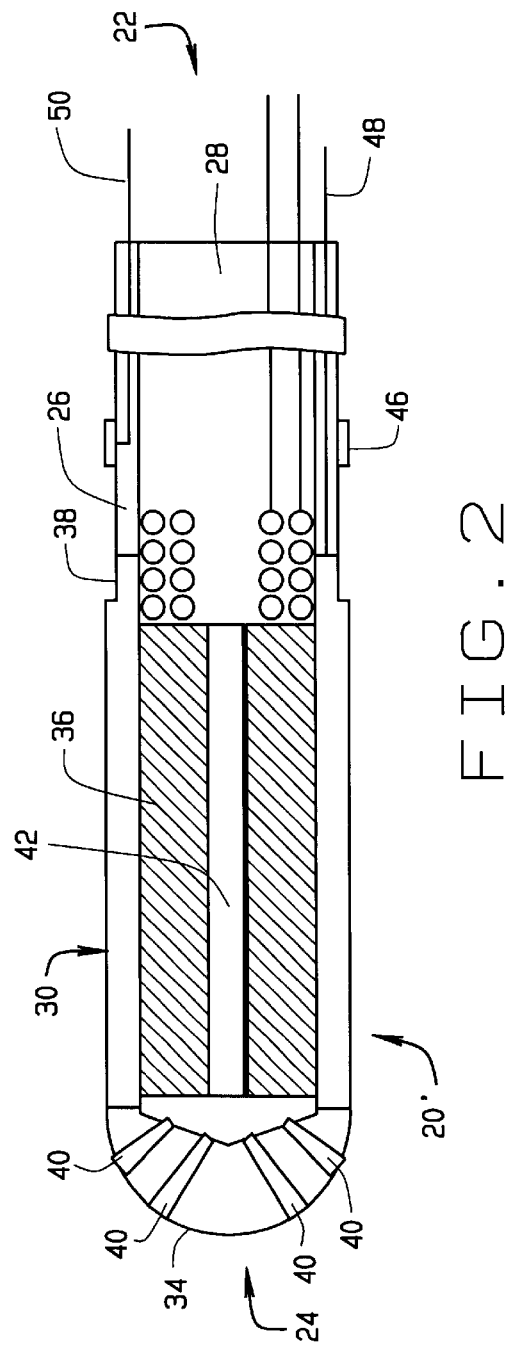

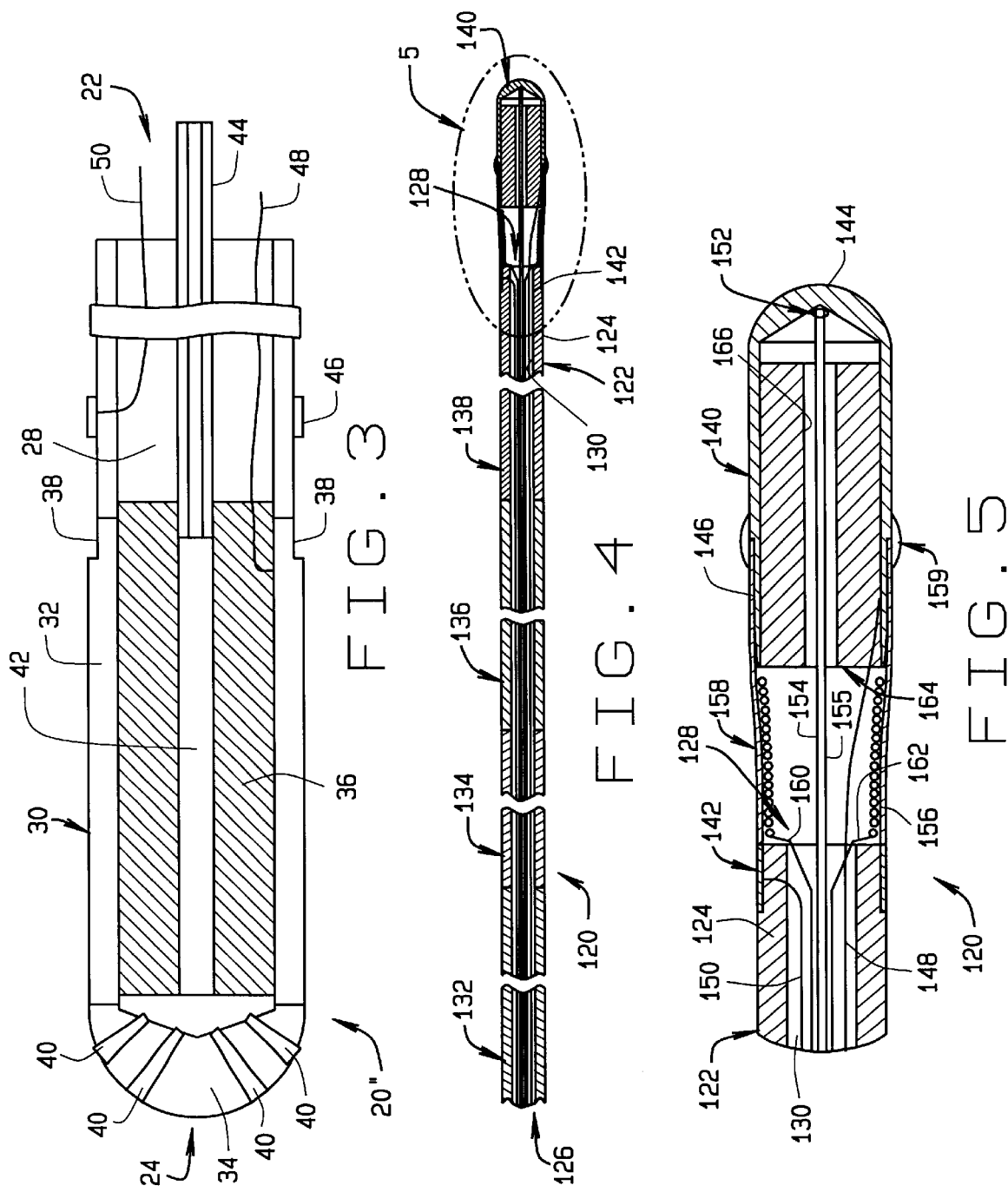

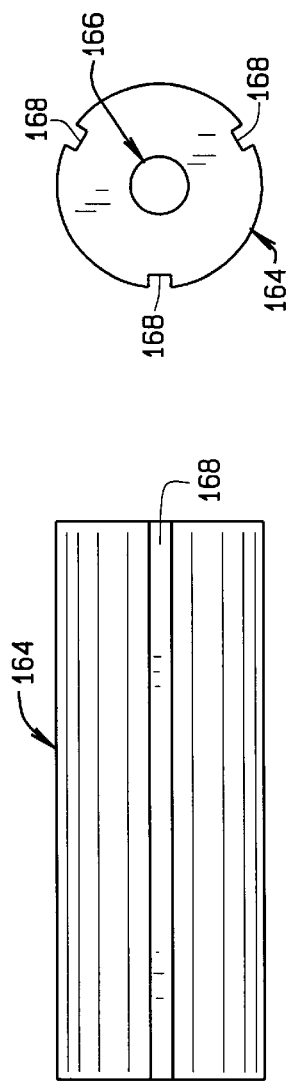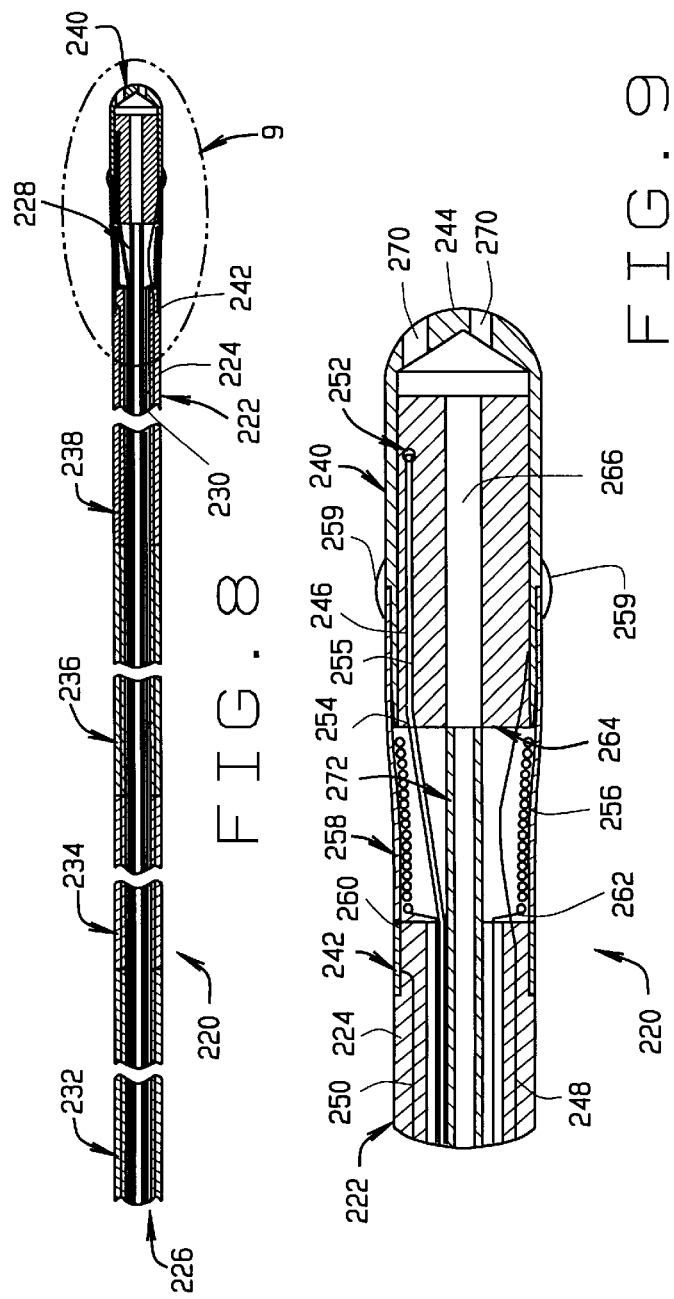

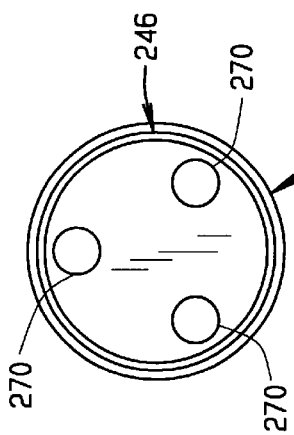
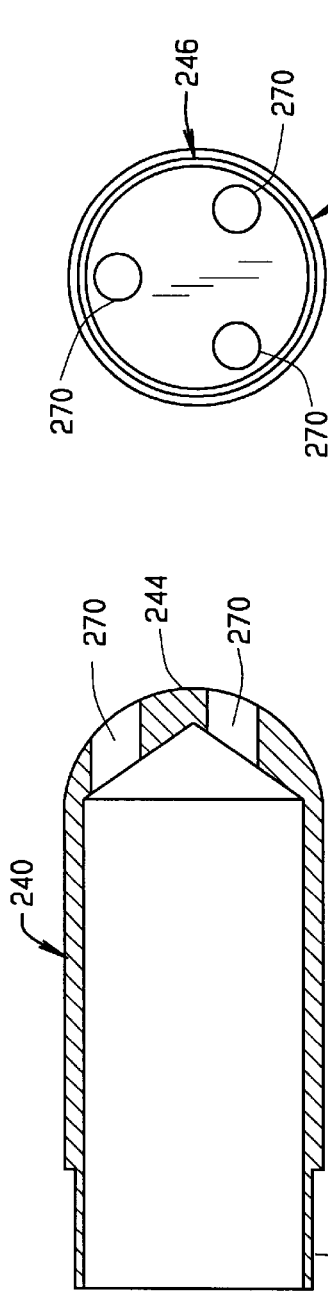
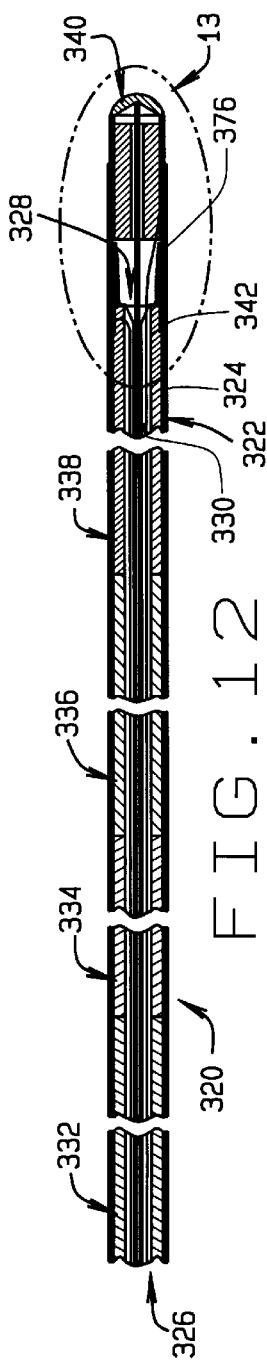
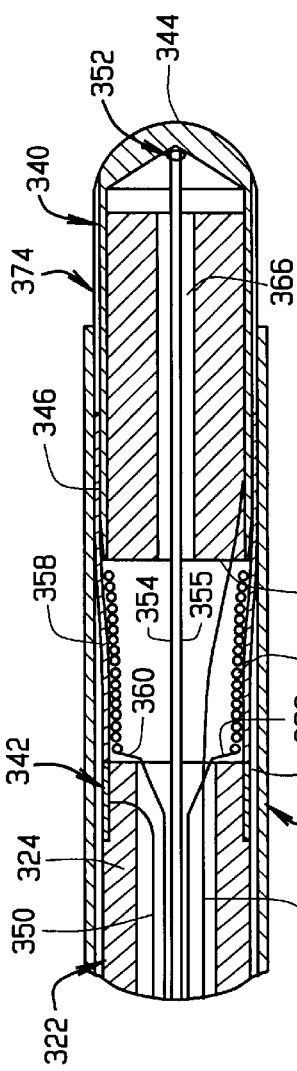

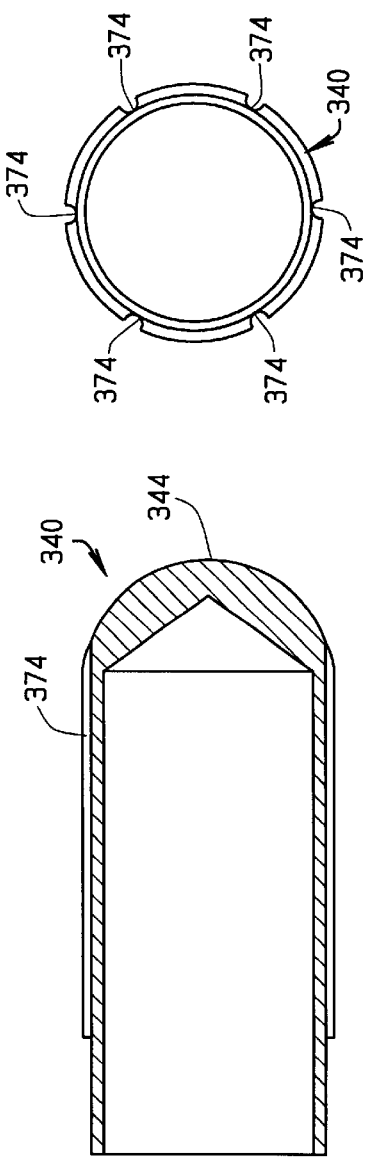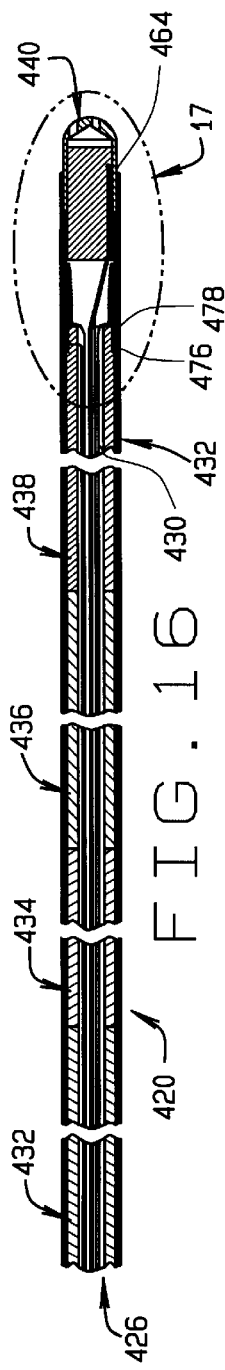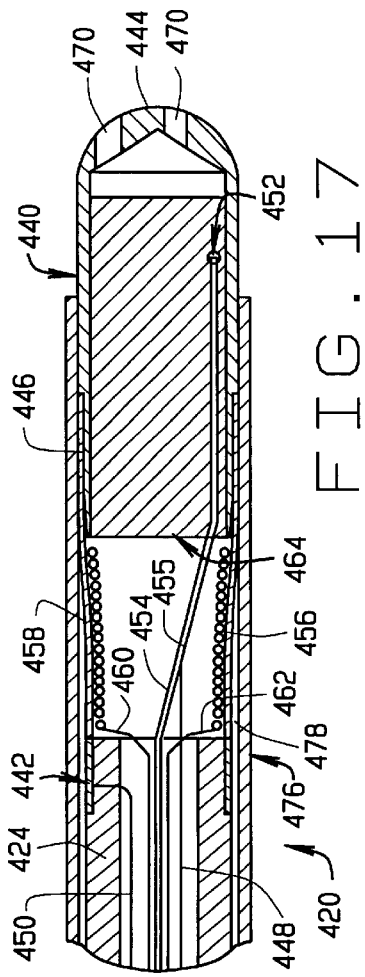

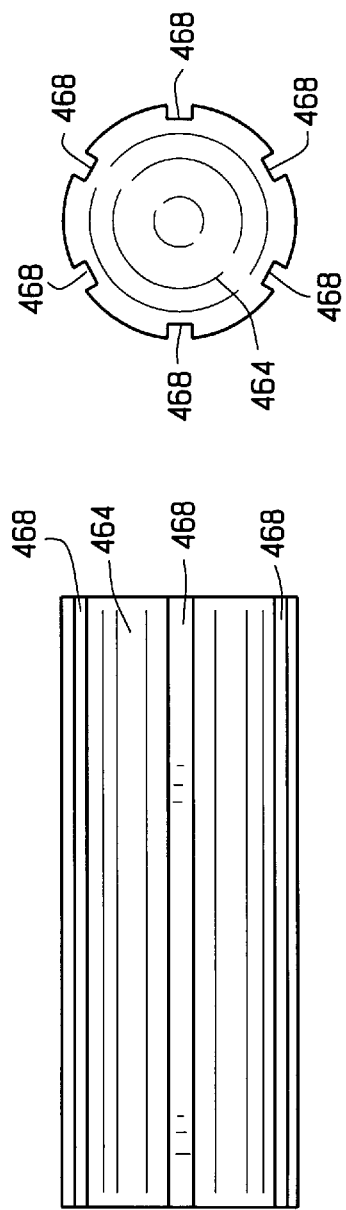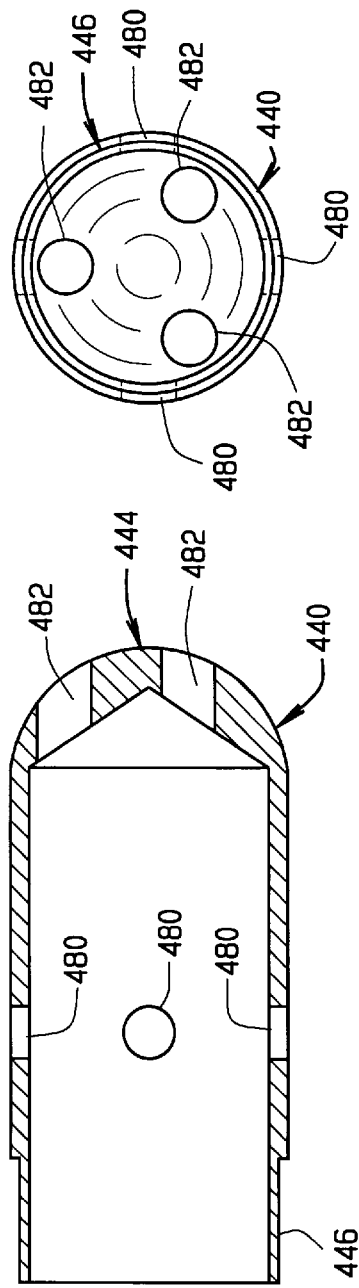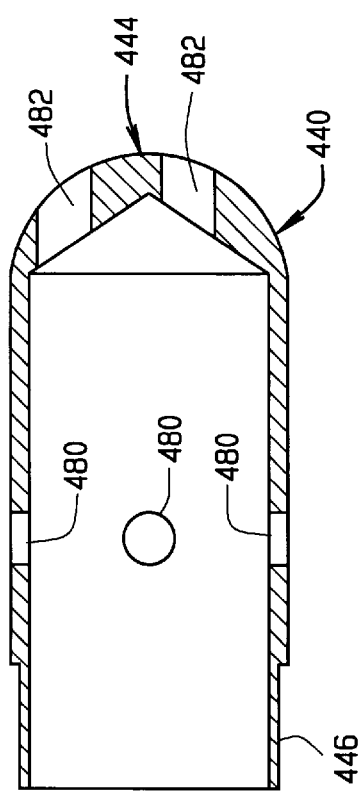

MAGNETICALLY GUIDABLE ELECTROPHYSIOLOGY CATHETER

CROSS-REFERENCE TO RELATED APPLICATION

This Application is a continuation-in-part application of U.S. patent application Ser. No. 09/771,954, filed Jan. 29, 2001 (incorporated herein by reference).

BACKGROUND OF THE INVENTION

This invention relates to electrophysiology catheters, and in particular to a magnetically guidable electrophysiology catheter.

Electrophysiology catheters are elongate medical devices that are introduced into the body and are used for sensing electrical properties of tissues in the body; applying electrical signals to the body for example for cardiac pacing; and/or applying energy to the tissue for ablation. Electrophysiology catheters have a proximal end, a distal end, and two or more electrodes on their distal end. Recently, electrophysiology catheters have been made with electrodes having openings in their distal ends for passage of normal saline solution which cools the surface tissues to prevent blood clotting. These electrodes can be difficult to navigate into optimal contact with the tissues using conventional mechanical pull wires.

SUMMARY OF THE INVENTION

The electrophysiology catheter of this invention is particularly adapted for magnetic navigation. The electrophysiology catheter comprises a tube having a proximal end and a distal end, and a lumen therebetween. The tube is preferably comprised of multiple sections of different flexibility, each section being more flexible than its proximal neighbor, so that the flexibility of the catheter increases from the proximal end to the distal end. A first generally hollow electrode member is located at the distal end of the tube. The first electrode has a generally cylindrical sidewall and a dome shaped distal end. There is a second electrode spaced proximally from the first electrode, and in general there are multiple ring electrodes spaced at equal distances proximal to the first electrode. In accordance with the principles of this invention, a magnetically responsive element is positioned at least partially, and preferably substantially entirely, within the hollow electrode member. The magnetically responsive element can be a permanent magnet or a permeable magnet. The magnet is sized and shaped so that it can orient the distal end of the catheter inside the body under the application of a magnetic field from an external source magnet. The magnet is preferably responsive to a magnetic field of 0.1 T, and preferably less. The magnet allows the distal end of the electrophysiology catheter to be oriented in a selected direction with the applied magnetic field, and advanced. Because the magnet is disposed in the hollow electrode, the distal end portion of the catheter remains flexible to facilitate orienting and moving the catheter within the body.

In accordance with one embodiment of the present invention, a temperature sensor, such as a thermistor or thermocouple is mounted in the distal end of the catheter for sensing the temperature at the distal end, for controlling the temperature of the catheter tip during ablation. With this embodiment, the rf energy delivered to the electrode can be adjusted to maintain a pre-selected tip temperature.

In accordance with another embodiment of the present invention, the end electrode is provided with a plurality of outlet openings, the magnetically responsive element has at least one passage therethrough, and a conduit is provided in the lumen to conduct irrigating fluid to the passage in the magnetically responsive element, which conducts the irrigating fluid to the end electrode where the fluid flows out the openings in the end electrode.

In accordance with another embodiment of the present invention, a sleeve is also provided around the tube, creating an annular space for conducting irrigating fluid to a point adjacent the end electrode.

In accordance with still another embodiment of the present invention, the end electrode is provided with a plurality of openings. The magnetically responsive element has a plurality of passages therein for conducting irrigating fluid delivered through a sleeve around the tube to the distal electrode tip, where it is discharged through holes in the tip.

BRIEF DESCRIPTION OF THE DRAWINGS

FIG. 1 is a longitudinal cross section of a first embodiment of a catheter constructed according to the principles of this invention;

FIG. 2 is a longitudinal cross section of a first alternate construction of the first embodiment of a catheter constructed according to the principles of this invention, adapted to deliver irrigating fluid to the distal end;

FIG. 3 is a longitudinal cross sectional view of a second alternate construction of the first embodiment of a catheter constructed according to the principles of this invention, showing a separate line for providing irrigating fluid to the distal end;

FIG. 4 is a longitudinal cross-sectional view of a second embodiment of an electrophysiology catheter constructed according to the principles of this invention;

FIG. 5 is a an enlarged longitudinal cross-sectional view of the distal end portion of the electrophysiology catheter of the second embodiment;

FIG. 6 is a side elevation view of the magnetically responsive element of the electrophysiology catheter of the second embodiment;

FIG. 7 is an end elevation view of the magnetically responsive element of the electrophysiology catheter of the second embodiment;

FIG. 8 is a longitudinal cross-sectional view of a third embodiment of an electrophysiology catheter constructed according to the principles of this invention;

FIG. 9 is an enlarged longitudinal cross-sectional view of the distal end portion of the electrophysiology catheter of the third embodiment;

FIG. 10 is an enlarged side elevation view of the end electrode of the third embodiment;

FIG. 11 is an enlarged rear end elevation view of the end electrode of the third embodiment;

FIG. 12 is a longitudinal cross-sectional view of a fourth embodiment of an electrophysiology catheter constructed according to the principles of this invention;

FIG. 13 is a an enlarged longitudinal cross-sectional view of the distal end portion of the electrophysiology catheter of the fourth embodiment;

FIG. 14 is an enlarged side elevation view of the end electrode of the fourth embodiment;

FIG. 15 is an enlarged rear end elevation view of the end electrode of the fourth embodiment;

FIG. 16 is a longitudinal cross-sectional view of a fifth embodiment of an electrophysiology catheter constructed according to the principles of this invention;

FIG. 17 is a an enlarged longitudinal cross-sectional view of the distal end portion of the electrophysiology catheter of the fifth embodiment;

FIG. 18 is an enlarged side elevation view of the magnetically responsive element of the fifth embodiment;

FIG. 19 is an enlarged end elevation view of the magnetically responsive element of the fifth embodiment;

FIG. 20 is an enlarged longitudinal cross-sectional view of the end electrode of the fifth embodiment; and FIG. 21 is an enlarged rear elevation view of the end electrode of the fifth embodiment.

Corresponding reference numerals indicate corresponding parts throughout the several views of the drawings.

DETAILED DESCRIPTION OF THE INVENTION

A first embodiment of an electrophysiology catheter constructed according to the principles of this invention is indicated generally as 20 in FIG. 1. The electrophysiology catheter 20 has a proximal end 22 and a distal end 24. The catheter 20 is preferably a hollow flexible tubular member comprising a sidewall 26 with a lumen 28 therethrough. The catheter 20 can be made from Pebax™.

The electrophysiology catheter 20 of the first embodiment has a first generally hollow electrode member 30 on its distal end 24. The electrode member 30 has a generally cylindrical sidewall 32 and a blunt, rounded dome-shaped distal end 34. In the preferred embodiment, the electrode member 30 is preferably about 0.250 inches long, and has an external diameter of about 0.1044 inches. According to the principles of this invention, the electrode member 30 is hollow, opening to the proximal end 22. In the preferred embodiment the electrode member has a cavity that is about 0.205 to about 0.210 inches long, with a diameter of between about 0.091 and 0.095 inches. A magnet member 36 is disposed substantially entirely within the electrode member 30. The magnet member 36 is preferably a solid cylindrical mass of a permanent magnetic material, such as Neodymium-Iron-Boron (Nd—Fe—B) or Samarium-Cobalt, or a permeable magnetic material, such as hiperco.

The proximal end portion 38 of the electrode 30 has a recessed diameter, facilitating joining the electrode 30 to the tube forming the catheter. In the preferred embodiment this recessed proximal d end portion 38 is about 0.05 inches long, and has an outside diameter of about 0.103 inches.

In a first alternate construction of the first preferred embodiment indicated generally as 20' in FIG. 2, there are a plurality of openings 40 in the dome 34, and there is at least one passage through the magnet member 36, such as passage 42 extending axially through the center of the magnet member 36, for the passage of irrigation fluid. The fluid can be provided through the lumen 28 of the catheter 20' as shown in FIG. 2, or in accordance with a second alternate construction 20" of the first preferred embodiment, a separate line 44 can be provided to provide irrigating fluid to the distal end 34 of the electrode 30 as shown in FIG. 3.

A second annular electrode 46 is positioned on the exterior sidewall 26 of the catheter 20, spaced proximally from the first electrode member 30. Lead wires 48 and 50 extend proximally from the electrodes 30 and 46. These lead wires can pass through the lumen 28 of the catheter (as shown in FIG. 3), or they can be embedded in the sidewall 26 (as shown in FIG. 2). The proximal ends of the lead wires 48 and 50 can be electrically connected to an apparatus for sensing the electrical potential between the electrodes, or to a device for applying an electric charge to the tissue between the electrodes, or to a device for applying electrical energy to the tissue for ablation between the tip electrode and a grounding pad on the patient.

By providing the magnet inside the first electrode, the distal end of the catheter remains more flexible, making it easier to navigate.

A second embodiment of a magnetically guidable electrophysiology catheter constructed according to the principles of this invention is indicated generally as 120 in FIGS. 4 and 5. The catheter 120 comprises a tube 122, having a sidewall 124, with a proximal end 126, a distal end 128, and a lumen 130 extending therebetween. The tube 122 is preferably comprised of a plurality of sections of different flexibility along its length. In this preferred embodiment, there are four sections 132, 134, 136, and 138, from the proximal end 126 to the distal end 128. Each section is preferably more flexible than the next most proximal section, so that the flexibility of the tube 122, and thus of the catheter 120, increases from the proximal end to the distal end. The sections 132, 134, 136, and 138 may be separate segments, joined together by ultrasonic welding or adhesive or other suitable means, or the sections 132, 134, 136 and 138 may be extruded in one continuous piece using a variable durometer extrusion process.

There is an end electrode 140 on the distal end of the electrophysiology catheter 120, and at least one ring electrode 142 on the distal end portion of the catheter, proximal to the end electrode. The end electrode 140 is preferably hollow, having a dome-shaped distal end 144. The proximal end of the electrode 140 has a section 146 of reduced outside diameter. The at least one ring electrode 142 is preferably a ring-shaped element extending circumferentially around the distal end portion of the tube 122. A lead wire 148 extends proximally from the end electrode 140, and a lead wire 150 extends proximally from the ring electrode 142. The lead wires extend to the proximal end of the catheter 120 through lumen 130 of tube 122 where they can be connected to devices for measuring electric signals in the tissue in contact with the electrodes, for providing pacing signals to the tissue in contact with the electrodes, and to apply ablative energy to the tissues in contact with the electrodes.

There is a temperature sensor, such as thermistor 152, on the distal end 126 of the catheter 120, for measuring the temperature at the distal end 144 of the end electrode 140. The thermistor 152 can be secured on an inside surface of the electrode 140 with an adhesive, and allows the temperature of the distal end of the electrode to be measured, and thus controlled. Lead wires 154 and 155 extend proximally from the thermistor 152 to the proximal end of the catheter 120 through lumen 130 of the tube 122 to provide temperature information for controlling the catheter tip temperature.

There is also at least one localization coil 156 in the distal end portion of the catheter 120 for locating the distal end of the catheter. The localization coil 156 is preferably disposed distally of the distal end 128 of the tube 122, and proximally of the end electrode 140. The localization coil 156 is enclosed in a jacket 158, that extends between the distal end 128 of the tube 122, and the proximal section 146 of the end electrode 140. The proximal end of the jacket 158 may be secured to the distal end 128 of the tube 122 by ultrasonic welding or an adhesive or other suitable means. The distal end of the jacket is friction fit over the proximal end of the electrode 140, and can be secured with a bead 159 of adhesive. The localization coil 156 receives electromagnetic signals from an array of transmitter coils located outside the patient. (Of course the transmitter coils could alternatively be located inside the patient, for example on a reference catheter, or the coils on the catheter could be transmitter coils, and the coils outside the patient or on the reference catheter could be receiver coils). Lead wires 160 and 162 extend proximally from the localization coil 156 to carry signals to the proximal end of the catheter 120, through lumen 130 in tube 122, to be processed to provide three dimensional location and orientation of the coil, and thus the distal end of the catheter 120.

There is a magnetically responsive element 164 in the distal end portion of the catheter 120. The magnetically responsive element 164 is preferably disposed at least partially, and preferably substantially entirely, inside the hollow end electrode 140. This reduces the stiffness of the distal end portion of the catheter 120. The magnetically responsive element 164 may be a body of a permanent magnetic material, such as neodymium-iron-boron (Nd—Fe—B), or a magnetically permeable material, such as iron. As shown in FIGS. 6 and 7, the magnetically responsive element 164 is preferably hollow, having a generally central passage 166. The lead wires 154 and 155 from the thermistor 152 extend through the passage 166 in the magnetically responsive element 164. There are a plurality of longitudinal grooves 168 in the exterior surface of the magnetically responsive element 164. As shown in FIG. 7, there are preferably three grooves 168 in the magnetically responsive element 164. The lead wire 148 passes through one of these grooves 168 to the end electrode 140. In the first preferred embodiment the magnetically responsive element is a generally cylindrical Nd—Fe—B magnet 0.240 inches long and 0.0885 inches in diameter. The passage 166 has a diameter of 0.023 inches.

A third embodiment of a magnetically guidable electrophysiology catheter constructed according to the principles of this invention is indicated generally as 220 in FIGS. 8 and 9. The catheter 220 comprises a tube 222, having a sidewall 224, with a proximal end 226, a distal end 228, and a lumen 230 extending therebetween. The tube 222 is preferably comprised of a plurality of sections of different flexibility along its length. In this preferred embodiment, there are four sections 232, 234, 236, and 238, from the proximal end 226 to the distal end 228. Each section is preferably more flexible than the next most proximal section, 50 that the flexibility of the tube 222, and thus of the catheter 220, increases from the proximal end to the distal end. The sections 232, 234, 236, and 238 may be separate segments, joined together by ultrasonic welding or adhesive or other suitable means, or the sections 232, 234, 236 and 238 may be extruded in one continuous piece using a variable durometer extrusion process.

There is an end electrode 240 on the distal end of the electrophysiology catheter 220, and at least one ring electrode 242 on the distal end portion of the catheter, proximal to the end electrode. The end electrode 240 is preferably hollow, having a dome-shaped distal end 244. The proximal end of the electrode 240 has a section 246 of reduced outside diameter. There are a plurality of openings 270 in the distal end 244 of the electrode 240. As shown in FIGS. 10 and 11 there are preferably three openings 270, extending generally axially through the end electrode 240. In this preferred embodiment, the end electrode 240 is about 0.250 inches long, with an outside diameter of about 0.104 inches, and an internal diameter of 0.0895 inches. The outside diameter of section 246 has an outside diameter of 0.096 inches, and is 0.050 inches long.

The at least one ring electrode 242 is preferably a ring-shaped element extending circumferentially around the distal end portion of the tube 222. A lead wire 248 extends proximally from the end electrode 240, and a lead wire 250 extends proximally from the ring electrode 242. The lead wires extend to the proximal end of the catheter 220, embedded in the sidewall 224 of the tube 222, where they can be connected to devices for measuring electric signals in the tissue in contact with the electrodes, for providing pacing signals to the tissue in contact with the electrodes, and to apply ablative energy to the tissues in contact with the electrodes 240 and 242.

There is a temperature sensor, such as thermistor 252, on the distal end of the catheter 220, for measuring the temperature adjacent the distal end 244 of the end electrode 240. The thermistor 252 can be secured on an inside surface of the electrode 240 with an adhesive, and allows the temperature of the electrode to be measured. Lead wires 254 and 255 extend proximally from the thermistor 252 to the proximal end of the catheter 220 through the lumen 230 of the tube 222 to provide temperature information for controlling the catheter.

There is also at least one localization coil 256 in the distal end portion of the catheter 220 for locating the distal end of the catheter. The localization coil 256 is preferably disposed distally of the distal end 228 of the tube 222, and proximally of the end electrode 240. The localization coil 256 is enclosed in a jacket 258, that extends between the distal end 228 of the tube 222, and the proximal section 246 of the end electrode 240. The proximal end of the jacket 258 may be secured to the distal end 228 of the tube 222 by ultrasonic welding or an adhesive or other suitable means. The distal end of the jacket is friction fit over the proximal end of the electrode 240, and can be secured with a bead 259 of adhesive. The localization coil 256 preferably receives electromagnetic signals from an array of transmission coils located outside the patient. Lead wires 260 and 262 extend proximally from the localization coil 256 in lumen 230 of tube 222 to carry signals to the proximal end of the catheter 220, to be processed to provide three dimensional location and orientation of the coil, and thus the distal end of the catheter 220.

There is a magnetically responsive element 264 in the distal end portion of the catheter 220. The magnetically responsive element 264 is preferably disposed at least partially, and preferably substantially entirely, inside the hollow end electrode 240. This reduces the stiffness of the distal end portion of the catheter 220. The magnetically responsive element 264 may be a body of a permanent magnetic material, such as neodymium-iron-boron (Nd—Fe—B), or a magnetically permeable material, such as iron. The magnetically responsive element 264 is preferably hollow, having a generally central passage 266. A conduit 272 extends through the lumen 230 of the tube 222 and connects to the generally central passage 266 of the magnetically responsive element 264 to deliver irrigating fluid to the distal end of the catheter 220, where it exits through the openings 270. If the lead wires from the electrodes, thermistor, and localization coil are embedded in the wall 224, then conduit 272 may not be necessary, as irrigation fluid can flow to the distal end of the catheter without contacting the lead wires, conversely, if the conduit 272 is present, the wires can pass through the lumen 230. The irrigating fluid cools the electrode 240 and the tissue in contact with the electrode 240. There are a plurality of longitudinal grooves in the exterior surface of the magnetically responsive element 264 (similar to grooves 168). There are preferably three grooves in the magnetically responsive element 264. The lead wire 248 passes through one of these grooves to the end electrode 240. The magnetically responsive element may be coated with an electrically thermally insulating material which also prevents fluid contact with the magnet surfaces. For this purpose, the tube 272 may pass through lumen 266 to insulate the inner surface of the magnetically responsive element. The lead wires 254 and 255 pass through another of the grooves. The magnetically responsive element 264 may be the same size and shape as the magnetically responsive element 164, described above.

A fourth embodiment of a magnetically guidable electrophysiology catheter constructed according to the principles of this invention is indicated generally as 320 in FIGS. 12 and 13. The catheter 320 comprises a tube 322, having a sidewall 324, with a proximal end 326, a distal end 328, and a lumen 330 extending therebetween. The tube 322 is preferably comprised of a plurality of sections of different flexibility along its length. In this preferred embodiment, there are four sections 332, 334, 336, and 338, from the proximal end 326 to the distal end 328. Each section is preferably more flexible than the next most proximal section, so that the flexibility of the tube 322, and thus of the catheter 320, increases from the proximal end to the distal end. The sections 332, 334, 336, and 338 may be separate segments, joined together by ultrasonic welding or adhesive or other suitable means, or the sections 332, 334, 336 and 338 may be extruded in one continuous piece using a variable durometer extrusion process.

There is an end electrode 340 on the distal end of the electrophysiology catheter 320, and at least one ring electrode 342 on the distal end portion of the catheter, proximal to the end electrode. The end electrode 340 is preferably hollow, having a dome-shaped distal end 344. The proximal end of the electrode 340 has a section 346 of reduced outside diameter. As shown in FIGS. 14 and 15, there are preferably a plurality of longitudinally extending grooves 374 in the external surface of the end electrode 340. In this preferred embodiment, there are six grooves 374 equally spaced about the circumference of the end electrode 340. In this preferred embodiment, the end electrode 340 is about 0.250 inches long, with an outside diameter of about 0.104 inches, and an internal diameter of 0.0895 inches. The outside diameter of section 346 has an outside diameter of 0.096 inches, and is 0.050 inches long.

The at least one ring electrode 342 is preferably a ring-shaped element extending circumferentially around the distal end portion 328 of the tube 322. A lead wire 348 extends proximally from the end electrode 340, and a lead wire 350 extends proximally from the ring electrode 342. Ring electrode 342 could be disposed on the outside of the sleeve 376 (discussed in more detail below). In that case the lead wire 350 extends through the wall 376, and the wall of the tube 322, into the lumen 330. The lead wires 348 and 350 extend to the proximal end 326 of the catheter 320 through the lumen 330 of the tube 322 where they can be connected to devices for measuring electric signals in the tissue in contact with the electrodes, for providing pacing signals to the tissue in contact with the electrodes, and to apply ablative energy to the tissues in contact with the electrodes.

There is a temperature sensor, such as thermistor 352, on the distal end 328 of the catheter 320, for measuring the temperature at the distal end 344 of the end electrode 340. The thermistor 352 can be secured on an inside surface of the electrode 340 with an adhesive, and allows the temperature of the distal end of the electrode to be measured. Lead wires 354 and 355 extend proximally from the thermistor 352, through the lumen 330 of the tube 322, to the proximal end of the catheter 320 to provide temperature information for controlling the catheter.

There is also at least one localization coil 356 in the distal end portion of the catheter 320 for locating the distal end of the catheter 320. The localization coil 356 is preferably disposed distally of the distal end 328 of the tube 322, and proximally of the end electrode 340. The localization coil 356 is enclosed in a jacket 358, that extends between the distal end 328 of the tube 322, and the proximal section 346 of the end electrode 340. The proximal end of the jacket 358 may be secured to the distal end 328 of the tube 322 by ultrasonic welding or an adhesive or other suitable means. The distal end of the jacket 358 is friction fit over the proximal end of the electrode 340. The localization coil 356 preferably receives electromagnetic signals from an array of transmitter coils located outside of the patient. Lead wires 360 and 362 extend proximally from the localization coil 356, through the lumen 330 of the tube 322, to carry signals to the proximal end of the catheter 320, to be processed to provide three dimensional location and orientation of the coil, and thus the distal end of the catheter 320.

There is a magnetically responsive element 364 in the distal end portion of the catheter 320. The magnetically responsive element 364 is preferably disposed at least partially, and preferably substantially entirely, inside the hollow end electrode 340. This reduces the stiffness of the distal end portion of the catheter 320. The magnetically responsive element 364 may be a body of a permanent magnetic material, such as neodymium-iron-boron (Nd—Fe—B), or a magnetically permeable material, such as iron. The magnetically responsive element 364 is preferably hollow, having a generally central passage 366. The lead wire 354 from the thermistor 352 extends through the passage 366 in the magnetically responsive element 364. There are a plurality of longitudinal grooves in the exterior surface of the magnetically responsive element 364. There are preferably three grooves in the magnetically responsive element 364. The lead wire 348 passes through one of these grooves to the end electrode 340. The magnetically responsive element 364 may be the same size and shape as the magnetically responsive element 64, described above.

A sleeve 376 surrounds all but the distal-most portion of the catheter 320, creating an annular space 378 through which irrigating fluid can be passed to cool the end electrode 340. The fluid passes through the annular space 378, and exits through the spaces formed between the grooves 374 in the end electrode 340 and the sleeve 376. Passage of fluid through the grooves 374 provides a more uniform distribution of cooling fluid, than if the grooves are omitted.

A fifth embodiment of a magnetically guidable electrophysiology catheter constructed according to the principles of this invention is indicated generally as 420 in FIGS. 16 and 17. The catheter 420 comprises a tube 422, having a sidewall 424, with a proximal end 426, a distal end 428, and a lumen 430 extending therebetween. The tube 422 is preferably comprised of a plurality of sections of different flexibility along its length. In this preferred embodiment, there are four sections 432, 434, 436, and 438, from the proximal end 426 to the distal end 428. Each section is preferably more flexible than the next most proximal section, so that the flexibility of the tube 422, and thus of the catheter 420, increases from the proximal end to the distal end. The sections 432, 434, 436, and 438 may be separate segments, joined together by ultrasonic welding or adhesive or other suitable means, or the sections 432, 434, 436 and 438 may be extruded in one continuous piece using a variable durometer extrusion process.

There is an end electrode 440 on the distal end of the electrophysiology catheter 420, and at least one ring electrode 442 on the distal end portion of the catheter, proximal to the end electrode. The end electrode 440 is preferably hollow, having a dome-shaped distal end 444. The proximal end of the electrode 440 has a section 446 of reduced outside diameter. As shown in FIGS. 20 and 21, there are a plurality of openings 480 in the side of the end electrode 440 and openings 482 in the distal end 444 of the end electrode.

The at least one ring electrode 442 is preferably a ring-shaped element and can extend circumferentially around the distal end portion of the. In that case the lead wire 448 extends proximally from the end electrode 440, and a lead wire 450 extends proximally from the ring electrode 442, through the wall of the sleeve 478 and the tube 422. The lead wires 448 and 450 extend through lumen 430 of the tube 422 to the proximal end of the catheter 420 where they can be connected to devices for measuring electric signals in the tissue in contact with the electrodes, for providing pacing signals to the tissue in contact with the electrodes, and to apply ablative energy to the tissues in contact with the electrodes.

There is a temperature sensor, such as thermistor 452, on the distal end of the catheter 420, for measuring the temperature at the distal end 444 of the end electrode 440. The thermistor 452 can be secured on an inside surface of the electrode 440 with an adhesive, and allows the temperature of the distal end of the electrode to be measured. Lead wires 454 and 455 extend proximally from the thermistor 452, through the lumen 430 of the tube 422, to the proximal end of the catheter 420 to provide temperature information for controlling the temperature of the catheter tip. Thermistor 552 can alternatively be a thermocouple or other temperature sensing device.

There is also at least one localization coil 456 in the distal end portion of the catheter 420 for locating the distal end of the catheter. The localization coil 456 is preferably disposed distally of the distal end 428 of the tube 422, and proximally of the end electrode 440. The localization coil 456 is enclosed in a jacket 458, that extends between the distal end 428 of the tube 422, and the proximal section 446 of the end electrode 440. The localization coil 456 preferably receives electromagnetic signals from an array of transmitter coils located outside of the patient's body. Lead wires 460 and 462 extend proximally from the localization coil 456, through lumen 430 of the tube 422, to carry signals to the proximal end of the catheter 420, to be processed to provide three dimensional location and orientation of the coil, and thus the distal end of the catheter 420.

There is a magnetically responsive element 464 in the distal end portion of the catheter 420. The magnetically responsive element 464 is preferably disposed at least partially, and preferably substantially entirely, inside the hollow end electrode 440. This reduces the stiffness of the distal end portion of the catheter 420. The magnetically responsive element 464 may be a body of a permanent magnetic material, such as neodymium-iron-boron (Nd—Fe—B), or a magnetically permeable material, such as iron. There are a plurality of longitudinal grooves 468 in the exterior surface of the magnetically responsive element 464. As shown in FIGS. 18 and 19, there are preferably six grooves 468 in the magnetically responsive element 464. The lead wire 448 and the lead wires 464 and 465 extend through one of the grooves 468.

A sleeve 476 surrounds all but the distal-most portion of the catheter 420, creating an annular space 478. Irrigating fluid can be passed through the annular space 478, and then into the openings 480 in the side of the end electrode 440. The fluid then passes through channels formed between the grooves 468 and the inside wall of the end electrode, where it can flow out the openings 482 in the distal end of the end electrode.

What is claimed is:

1. An electrophysiology catheter having a proximal end and a distal end, at least one electrode adjacent the distal end, a lead wire extending proximally from the at least one electrode, a magnetically responsive element in the distal end portion of the catheter, the catheter having at least two sections of different flexibility, each section being more flexible than the next most proximal section so that the flexibility of the catheter increases from the proximal end to the distal end, wherein the at least one electrode includes an end electrode having a plurality of longitudinally extending grooves, and further comprising an external sleeve defining an annular space terminating at the end electrode, the grooves in the end electrode and the sleeve defining a plurality of channels for ejecting irrigating fluid conducted in the annular space.

2. An electrophysiology catheter having a proximal end and a distal end, at least one electrode adjacent the distal end, a lead wire extending proximally from the at least one electrode, a magnetically responsive element in the distal end portion of the catheter, the catheter having at least two sections of different flexibility, each section being more flexible than the next most proximal section so that the flexibility of the catheter increases from the proximal end to the distal end, wherein the at least one electrode includes a hollow end electrode on the distal end of the catheter, having a plurality of openings therein, wherein the magnetically responsive element is located at least partially in the end electrode and has at least one passage therein for the passage of irrigating fluid to allow irrigating fluid to be delivered from the openings in the end electrode, and wherein the at least one passage in the magnetically responsive element comprises at least one longitudinally extending groove in the exterior of the magnetically responsive element.

* * * * *